US011180707B2

(12) United States Patent
Faramarzi et al.

(10) Patent No.: US 11,180,707 B2
(45) Date of Patent: Nov. 23, 2021

(54) SYSTEM AND METHOD FOR DUPLICATING FLAMMABLE GAS

(71) Applicants: Faramaz Fred Faramarzi, Encino, CA (US); Sabrina Faramarzi, Encino, CA (US); Sandra Faramarzi, Encino, CA (US)

(72) Inventors: Faramaz Fred Faramarzi, Encino, CA (US); Sabrina Faramarzi, Encino, CA (US); Sandra Faramarzi, Encino, CA (US)

( * ) Notice: Subject to any disclaimer, the term of this patent is extended or adjusted under 35 U.S.C. 154(b) by 257 days.

(21) Appl. No.: 16/529,626

(22) Filed: Aug. 1, 2019

(65) Prior Publication Data

US 2020/0056110 A1 Feb. 20, 2020

Related U.S. Application Data

(60) Provisional application No. 62/714,479, filed on Aug. 3, 2018.

(51) Int. Cl.

| | |
|---|---|
| ***C10L 3/08*** | (2006.01) |
| ***F17C 11/00*** | (2006.01) |
| ***C12M 1/107*** | (2006.01) |
| ***F17C 6/00*** | (2006.01) |
| *F17C 13/02* | (2006.01) |

(52) U.S. Cl.

CPC ............... *C10L 3/08* (2013.01); *C12M 21/04* (2013.01); *F17C 6/00* (2013.01); *F17C 11/007* (2013.01); *C10L 2200/0476* (2013.01); *C10L 2290/30* (2013.01); *F17C 13/025* (2013.01); *F17C 2205/0323* (2013.01); *F17C 2205/0338* (2013.01)

(58) Field of Classification Search

CPC ......... C10L 2200/0476; C10L 2290/26; C10L 3/08; C12M 21/12; C12M 21/04; C12M 43/02

See application file for complete search history.

(56) References Cited

U.S. PATENT DOCUMENTS

| | | | | |
|---|---|---|---|---|
| 2,822,888 | A | 2/1958 | MacLaren | |
| 4,077,779 | A | 3/1978 | Sircar et al. | |
| 3,150,942 | A | 9/1984 | Srini | |
| 4,553,981 | A | 11/1985 | Fuderer | |
| 4,869,894 | A | 9/1989 | Wang et al. | |
| 4,963,339 | A | 10/1990 | Krishnamurthy et al. | |
| 5,229,089 | A | 7/1993 | Ramachandran et al. | |
| 7,135,308 | B1 * | 11/2006 | Bush | C12P 7/06 435/42 |
| 2007/0048848 | A1 * | 3/2007 | Sears | C12M 33/10 435/134 |
| 2008/0257719 | A1 | 10/2008 | Suratt | |
| 2010/0151540 | A1 * | 6/2010 | Gordon | B01F 5/0646 435/134 |

(Continued)

*Primary Examiner* — Imran Akram

(74) *Attorney, Agent, or Firm* — Patent Law Inc

(57) ABSTRACT

A system and method for duplicating a flammable gas (SDFG) that utilizes a specially engineered liquid in combination with a purpose-built container to duplicate the flammable gas is disclosed. There are three methods for the production of an engineered liquid for use in the system. In less than one hour, a single unit of any flammable or hydrocarbon gas will yield up to at least double the quantity of the same gas back.

2 Claims, 3 Drawing Sheets

(56) References Cited

U.S. PATENT DOCUMENTS

| | | | | |
|---|---|---|---|---|
| 2010/0233761 | A1* | 9/2010 | Czartoski | C12N 13/00 435/71.1 |
| 2014/0093951 | A1* | 4/2014 | Hassan | C12M 21/02 435/292.1 |
| 2017/0051230 | A1* | 2/2017 | Hassan | B01F 13/1016 |
| 2017/0051244 | A1* | 2/2017 | Hassan | C12P 7/6463 |

* cited by examiner

| METHOD FOR PRODUCTION OF AN ENGINEERED LIQUID | | | | | | | | | |
|---|---|---|---|---|---|---|---|---|---|
| Percentage of ingredients to produce 1,000 liters of engineered liquid | | | | | | | | | |
| | First week to stimulate and culture | | | | Second week to enhance and multiply | | | | |
| | Stage one | | | | Stage two / mix and wait for one week | | | | Stage 3 |
| Liter production | Bacteria | Algae | Water | Mix well and Sit for one week | Either Brown glue | OR Bone powder | Mix with water for 30 Min. and strain | Sugar or sugar substitute | At the end of the second week, strain mixture from stage 2, then add water up to 1000 liters |
| 1000 | 50 g | 100 g | 1 liter | | 2 kg | 5 kg | 10 Liter | 10 kg | |

Fig. 2

SYSTEM AND METHOD FOR DUPLICATING FLAMMABLE GAS

TECHNICAL FIELD

The invention generally pertains to the production of flammable gas, and more particularly to a system that includes multiple methods that utilize a container in which Deoxygenated or ambient air, or nitrogen gas (DAANG) passes through an engineered liquid to duplicate a selected/introduced flammable gas.

BACKGROUND ART

Flammable gasses are gasses that burn in the presence of an oxidant when provided with a source of ignition. The risk of ignition increases in relation to the amount of gas present. If the concentration of a flammable gas in an environment exceeds the upper explosive limit (UEL), the environment becomes 'too rich to burn', which creates the opposite effect, instead reducing a chance of ignition.

Flammable gasses can be produced both naturally and artificially. Natural gases, like Biogas or Methane, are generally created from decaying organic matter. These same chemicals can also be created in a lab setting through a chemical process.

Both the natural and artificial method of natural gas production have drawbacks, including but not limited to: maintenance; monitoring; strong, pungent odors; dangerous bacteria; decaying matter; byproducts; issues with capturing the gasses; issues with storing the gasses; the lengthy process for producing, capturing, storing, purifying, and overall creating a useable natural gas product; and cost.

Gas and energy companies developed an infrastructure based on the two most common forms of flammable gasses: natural gas and coal based gas, which is what the energy industry currently runs on. The majority of natural gas is Methane ($CH_4$), which is also a byproduct of petroleum and other fossil fuels. However, Methane is rarely found in a solely pure form in nature, usually found in conjunction with other hydrocarbons including, but not limited to: Butane, Ethane, and Propane. Manufactured coal gas, and its several variants, was commonly used in the 19th century and beyond. The simpler process consists of heating coal, or other similar organic substances, to produce a flammable gas. The resulting gas is a combination of carbon monoxide (CO), hydrogen (H) and other gasses depending upon the exact process and staring substances. This method has long been utilized due to the comparative ease of procuring coal and therefore producing coal based gas. These gases have long proven to be consistent fuel sources for residential, commercial, and industrial energy needs and endeavors.

The discovery of massive natural gas fields in Southwestern America, in conjunction with technological advancements in long distance pipeline construction, dramatically altered the gas industry moving into the twentieth century. The sheer volume of gas fields emphasized a need for advancements in the natural gas infrastructure, materials, purification, and technology fields.

In the time period surrounding World War II, a second era of rapid gas industry growth occurred, with a national market for national gas consumption emerging. During the last half of the twentieth century, natural gas consumption in the United States ranged from about 20-30% of total national energy utilization.

The natural gas industry is not without its issues. First, there are periodic shortages of natural gas due to a variety of factors, ranging from regulatory issues to OPEC oil embargos to increased general needs. While it is the cleanest burning of all fossil fuels, natural gas exists in limited supply. Estimates of future natural gas availability vary widely, from mere hundreds to several thousands of years. Such estimates are dependent upon the technology that must be developed to produce natural gas. Currently, natural gas is the most economically efficient source of energy used throughout the world. A multitude of natural and flammable gases are used annually to power homes, factories and automobiles. These natural gases are also used in power plants to produce electricity and other forms of power.

Second, the extraction methods for obtaining these flammable gasses have an impact on the environment. There are several common places to extract and obtain flammable gases: coal bed methane (CBM), gas shale, natural gas from oil wells from sand (tight gas), gas hydrates (clathrates), fossil fuels, and extraction of fuel from $CO_2$. In addition, there are plant-based technologies, such as from corn. Many others are in the research and development stage. Presently, all of the available methods and sources have a high cost of production and present extreme challenges. These include the actual cost of extraction, the damage to the environment, transportation and logistical strategies to get the fuel to the final destination.

From start to finish, the process of obtaining natural gas is extensive and invasive. For example, to capture hydrocarbon gas from a natural gas reserve initially requires deep drilling to find the reservoir, capturing the gas as it is expelled from the underground pocket, and transferring the crude gas to a refinery. At that refinery, the gas is separated into its parts (for example: propane, methane, butane, and a bevy of other chemicals or substances may all be present in the sample obtained when only methane is wanted or needed). The separated gases are then individually stored and transferred to customer either by gas tankers or through built in gas line infrastructure, which are both relatively costly methods. Further, those separated gases are not all necessarily needed; some are too harmful to use, some are scarce, some are overproduced, and some are entirely unnecessary.

These final product natural gas fuels and natural-gas condensate consist of several hydrocarbon gases. The most common condensates consist of a combination of: butane; cyclobutene; cycloheptane; cyclohexane; cyclopentane; cyclopropane; dimethylpropane; ethane; Ethylene; heptane; hexane; methane; methyl butane; methanol, methyl propane; pentane; propane, and/or other hydrocarbon flammable gases.

In general, the major costs associated with natural gas production do not originate from the initial drilling and securing of the gas but instead with the transfer, refinement, and storage of the gas. These costs are relayed to the final consumer and prove a major burden. The necessity for storage, transportation, and infrastructure is a multi-billion dollar industry.

On some oil and natural gas drilling sites, natural gases are simply left to burn when they are not desired, which causes other environmental issues as well as incurring additional economical concerns, as related to cleanup.

The instant invention offers a solution to these problems by providing a system, method, and container by which a quantity of almost any introduced flammable gas can be quickly and easily produced by the instant invention's process that utilizes the instant invention's engineered bacteria liquid which is capable of duplicating such a flammable gas within the instant invention's container.

PRIOR ART

A search of the prior art did not disclose any literature or patents that read directly on the claims of the instant invention. For background purposes and indicative of the art to which the invention relates, reference may be made to the following remaining patents found in the patent search. However, the following U.S. patents are considered related:

| U.S. PAT. NO. | INVENTOR | ISSUED |
|---|---|---|
| 4,869,894 | Wang, et al | Sep. 26, 1989 |
| 5,229,089 | Ramachandran, et al | Jul. 20, 1993 |
| 2008/0257719 | Suratt | Oct. 23, 2008 |
| 2,822,888 | MacLaren | Feb. 11, 1958 |
| 3,150,942 | Srini | Sep. 29, 1984 |
| 4,077,779 | Sircar, et al | Mar. 7, 1978 |
| 4,553,981 | Fuderer | Nov. 19, 1985 |
| 4,963,339 | Krishnamurthy, et al | Oct. 16, 1990 |

DISCLOSURE OF THE INVENTION

The primary object of the invention is to provide a system for duplicating a flammable gas utilizing a purpose-built container that holds a proprietary engineered liquid, through which Deoxygenated or ambient air, or nitrogen gas (DAANG) passes through and escapes in the form of bubbles carrying a flammable gas which is duplicated from the same type of flammable gas that was introduced to the engineered liquid within the container.

In addition to the primary object, it is also an object of the invention to provide a system for duplicating a flammable gas utilizing a purpose-built container that:

is easy to use, is reliable and durable, is easy to maintain and clean, can be made in various sizes, allows multiple types of gases to be duplicated consecutively, allows flammable gas producers to save over fifty percent at final production cost, can produce at least an equal amount of an introduced gas volume, can be utilized in any city in the world, on any scale, allows one preselected gas to be produced with the exact kind of gases independently and at a destination location, reduces refinery costs along with the associated refinery process waiting period, allows gas companies to reduce the need to transport gas through expensive pipelines by ship, or by truck, allows storage needs to be lessened or eliminated.

reduces the need for drilling, capturing gases and risk of explosion, and allows less drilling to be required and less unwanted gases that are released into the environment, lessening environment pollution.

These and other objects and advantages of the present invention will become apparent from the subsequent detailed description of the preferred embodiment and the appended claims taken in conjunction with the accompanying drawings.

The primary object of the invention is to provide a method for the production of an engineered liquid that is capable of duplication of a flammable gas. In addition to the primary object, it is also an object of the invention to provide an engineered liquid that:

allows flammable gas producers to save at least fifty percent at final production cost, can be utilized in any city in the world, on any scale, allows one preselected gas to be produced with the exact kind of gases independently and at a destination location, allows a customer to consecutively produce multiple flammable gases, reduces refinery costs along with the associated refinery process waiting period, allows gas companies to extensively reduce need to transport gas through expensive pipelines, by ship, or by truck, allows storage needs to be lessened or eliminated, extensively reduces the need for drilling, capturing gases, and risk of explosion, extensively allows less drilling to be required and less unwanted gases that are released into the environment, lessening environmental pollution, produces only the desired gas, unlike a conventional natural gas refinery process in which many unwanted or hazardous gases are separated as part of the process, allows the life expectancy of available natural gases to be increased by up to four times.

These and other objects and advantages of the present invention will become apparent from the subsequent detailed description of the preferred embodiment and the appended claims taken in conjunction with the accompanying drawings.

The primary object of the invention is to provide a system for duplicating flammable gas that allows various quantities of hydrocarbon flammable gas to be quickly duplicated and produced using relatively simple components and materials.

In addition to the primary object to the invention, it is also an object of the invention to provide a system for duplicating a flammable gas that:

allows flammable gas producers to save at least fifty percent at final production cost, can product at least two times an introduced gas volume, can be utilized in any city in the world, on any scale, allows one preselected gas to be produced with the exact kind of gases independently and at a destination location, allows a customer to consecutively produce multiple flammable gases, reduces refinery costs along with the associated refinery process waiting period, allows gas companies to reduce need to transport gas through expensive pipelines by ship or by truck, allows storage needs to be lessened or eliminated, reduces the need for drilling, capturing gases, and risk of explosion, allows less drilling to be required and less unwanted gases that are released into the environment, lessening environment pollution, produces only the desired gas, unlike a conventional natural gas refinery process in which any unwanted or hazardous gases are separated as part of the process, allows the life expectancy of available natural gases to be increased by at least two times These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 2 is a table with the ratios necessary to engineer one thousand (1000) liters of an engineered liquid.

SUMMARY OF THE INVENTION

A system and method for duplicating a flammable gas (SDFG) that utilizes a specially engineered liquid in combination with a purpose-built container to duplicate the flammable gas is disclosed. In a particular embodiment, the flammable gas is from the hydrocarbon family of flammable gasses, including but not limited to Butane, Cyclobutane, Cycloheptane, Cyclopentane, Cyclopropane, Dimethylpropane, Ethane, Heptane, Hexane, Methane, Methyl Butane, Methanol, Methyl Propane, Pentane, Propane and other hydrocarbon based flammable gases. It is envisioned that this process, method and container can apply to all flammable gasses.

Figure 1:
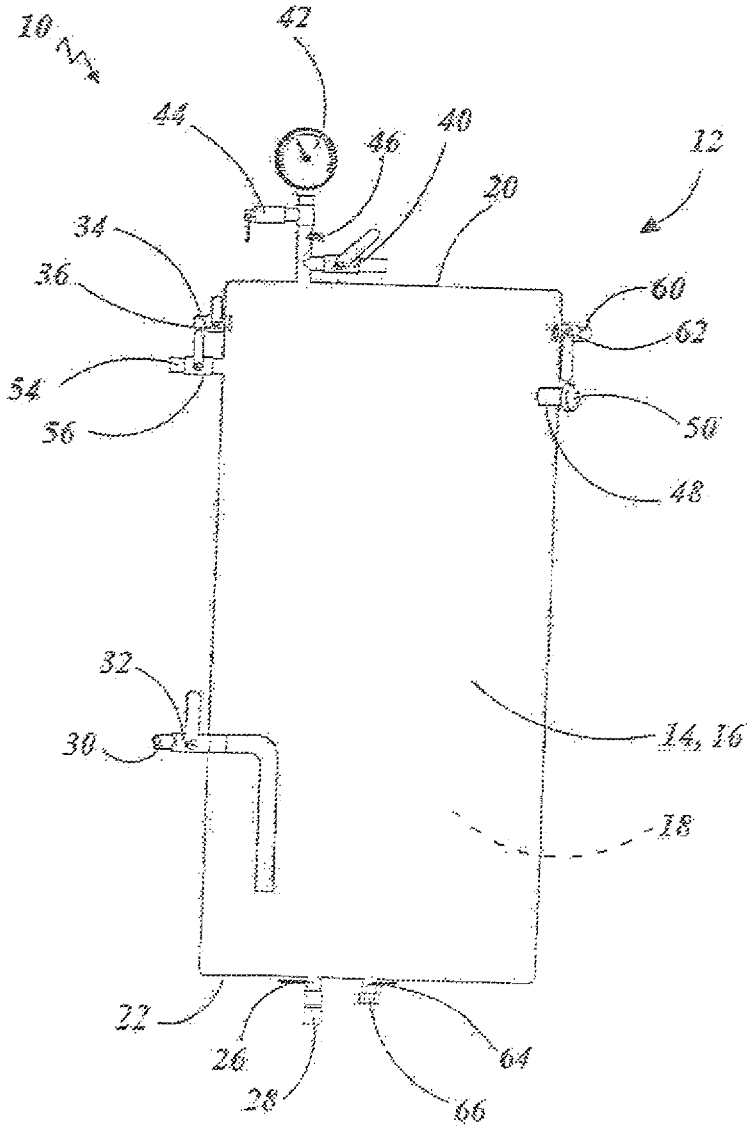
FIG. 1 is an elevational view showing a container used in a system for duplicating a flammable gas.

A system for duplicating a flammable gas (SDFG), as shown in FIG. 1, that utilizes a structure comprising a portable or stationary container capable of holding gas and liquid. The container is purpose-built to facilitate the duplication of a hydrocarbon or other flammable gas by use of a proprietary engineered liquid that comprises mutated and cultured bacteria, along with other ingredients. DAANG passes through the engineered liquid within the container and escapes in the form of bubbles carrying the flammable gas. The SDFG can duplicate at least equal the amount of a flammable gas that is introduced to the engineered liquid.

The SDFG 10, a container 14 has: an outer side surface 16; an inner side surface 18; an upper surface 20; a lower surface 22; an air inlet 26 comprising a control valve 28 for entrance of deoxygenated or ambient air, or nitrogen gas (DAANG); a gas inlet 34 comprising a control valve 36 for entrance of a flammable gas; an air pressure gauge 42; a liquid entrance opening 48 that allows engineered liquid to be placed into the container; a first gas outlet 54 comprising a control valve 56 for release of gas; a second gas outlet 60 that functions as a final release of any remaining gas; and a drainage outlet 64 comprising a control valve 66.

In a particular embodiment, the container is made of material selected from the group consisting of metal, glass, plastic, concrete, wood, and a composite. In a particular embodiment, the liquid entrance opening 48 further comprises a sealing mechanism 50.

In a particular embodiment, a SDFG 10, the container 14 has: an outer side surface 16; an inner side surface 18; an upper surface 20; a lower surface 22; an air inlet 26 for entrance of air into the container, the air inlet opening comprising a control valve 28; a gas inlet 34 for entrance of a flammable gas into the container, the gas inlet opening comprising a control valve 36; an air pressure gauge 42 comprising a warning sensor 44, a control valve 40, and a fuse 46; a liquid entrance opening 48 comprising a sealing mechanism 50; a first gas outlet 54 for release of the flammable gas, the first gas outlet comprising a control valve 56; a second gas outlet 60 for final release of the remaining gas, the second gas outlet comprising a control valve 62; a drainage outlet 64 for release of liquid after use, the drainage outlet comprising a control valve 66.

The air inlet, the gas inlet, the air pressure gauge, liquid entrance opening, and first and second gas outlets are combined into a single multi-function mechanism 70 comprising a rotating valve 72. In a particular embodiment, the air is comprised of DAANG. In a particular embodiment, the first air inlet is configured on the container's lower surface, allowing the DAANG to enter from a lower area of the container and to form bubbles that rise through liquid within the container; or the first air inlet is configured on the container's side surface, adjacent the container's lower surface. In a particular embodiment, the sensors and automatic valves 68 are configured to fully automate operation of the system, or the sensors and automatic valve 68 are configured to substantially automate operation of the system. In a particular embodiment, the fuse is configured to provide release of above-limit pressure in container. The container further comprises an air dispersing means 76 that distribute and combine DAANG, bubbles and bacteria within the container. In a particular embodiment, the container further comprises a frame 78 configured to surround and support the container, the frame comprising an upper member 80, a lower member 82, and at least two vertical members 84 extending from the upper member to the lower member and longitudinally on the side of the container.

There are three methods for the production of an engineered liquid for use in a system to duplicate a flammable gas disclosed. The engineered liquid facilitates duplicating a quantity of almost any selected or desired flammable gas.

The method comprises the following steps: place a bacteria mixture into a container; add an algae mixture into the container; add water to the bacteria and algae mixture to create a mutated bacteria solution; add a quantity of bone powder; add a quantity of nutrients and water; and allow the mutated bacteria solution to culture.

The method for producing an engineered liquid, wherein a bacteria is originally in a dormant state; is derived from organic matter; and is a powder. The method for producing an engineered liquid, wherein the water added is room temperature. The mutated bacteria solution is created by adding water to the bacteria mixture and the algae mixture in the container to activate the bacteria mixture and algae mixture to react with each other. The mutated bacteria solution is stored at a temperature ranging from 5°-45° Celsius and is non flammable.

The method for producing an engineered liquid, wherein the amount of the bacteria mixture added is according to the formula in FIG. 2. The method for producing an engineered liquid, wherein the algae mixture is dormant; is derived from green algae, red algae, cyanobacteria, and other edible forms of algae; and is a powder. The method for producing an engineered liquid, wherein the amount of the algae mixture added is according to the formula in FIG. 2. The water is added to increase the amount of the engineered liquid to a desired volume and the amount of water added is according to the formula in FIG. 2. The method for producing an engineered liquid, wherein the bone powder is produced by heating animal by-products to their boiling point then grinding the resulting mixture to a fine powder or the bone powder is produced by heating animal bones to their boiling point then grinding the resulting mixture to a fine powder. The method for producing an engineered liquid, wherein the bone powder is a powder or a liquid or a gelatinous mixture. The nutrients consist of glucose, glucose derived substances, sugar, sugar derived substances, or organic by-products or materials. The amount of water added to the mutated bacteria solution is according to the formula in FIG. 2. The engineered liquid solution is capable of replicating and producing a flammable gas and is first introduced to a flammable gas, then introduced to Deoxygenated or Ambient Air or Nitrogen Gas (DAANG) to extract, carry out, and transfer the flammable gas from the engineered liquid.

The method for producing one thousand (1000) liters of an engineered liquid, comprising the following steps: Stage one: add fifty (50) grams of bacteria to a container; add one hundred (100) grams of algae to the container; add one (1) liter of water to the container; mix the bacteria, the algae, and the water; allow the mixture to sit for one week to create a mutated bacteria mixture; Stage two: add five (5) kilograms of bone powder or two (2) kilograms of brown glue mixed with ten (10) liters of water to the mutated bacteria mixture; add ten (10) kilograms of sugar; allow the mixture to sit for one week to create the engineered liquid; Stage 3: strain the engineered liquid for purity, keeping the liquid; and add water, as needed, to reach one thousand (1000) liters.

The bacteria and algae are originally in dormant states; are derived from organic matter; and are powders. The mutated bacteria solution is stored at a temperature ranging from 5°-45° Celsius. Water is added to increase the amount of the engineered liquid to the desired volume. The engineered liquid is also stored at a temperature ranging from 5°-45° Celsius and is non flammable.

The method of introduction of DAANG is by passing the flammable gas through the engineered liquid. The flammable gas is from the hydrocarbon family of flammable gasses or other flammable gasses. The algae is derived from green algae, red algae, cyanobacteria, and other edible forms of algae. The water is purified by boiling then cooling the liquid. Five (5) kilograms of bone powder can be replaced with two (2) kilograms of bone glue; and the bone powder is produced by heating animal by-products to their boiling point then grinding the resulting mixture to a fine powder or by heating animal bones to their boiling point then grinding the resulting mixture to a fine powder. The bone powder is a powder or a liquid or a gelatinous mixture; and the sugar is sugar, a sugar derived substance, glucose, or glucose derived substance or an organic by-products or material. The engineered liquid solution is capable of replicating and producing a flammable gas. The engineered liquid is first introduced to a flammable gas, then introduced to DAANG to extract, carry out, and transfer the flammable gas from the engineered liquid. The method of introduction of DAANG is by passing the flammable gas through the engineered liquid.

In a particular embodiment, in less than one hour, a single unit of any flammable or hydrocarbon gas will yield up to at least double the quantity of the same gas back. DAANG in combination with the engineered liquid and a desired hydrocarbon flammable gas within a specially designed container will result in production of at least two times more of the same originally introduced hydrocarbon gas and the increased volume of flammable gas.

Figure 3:
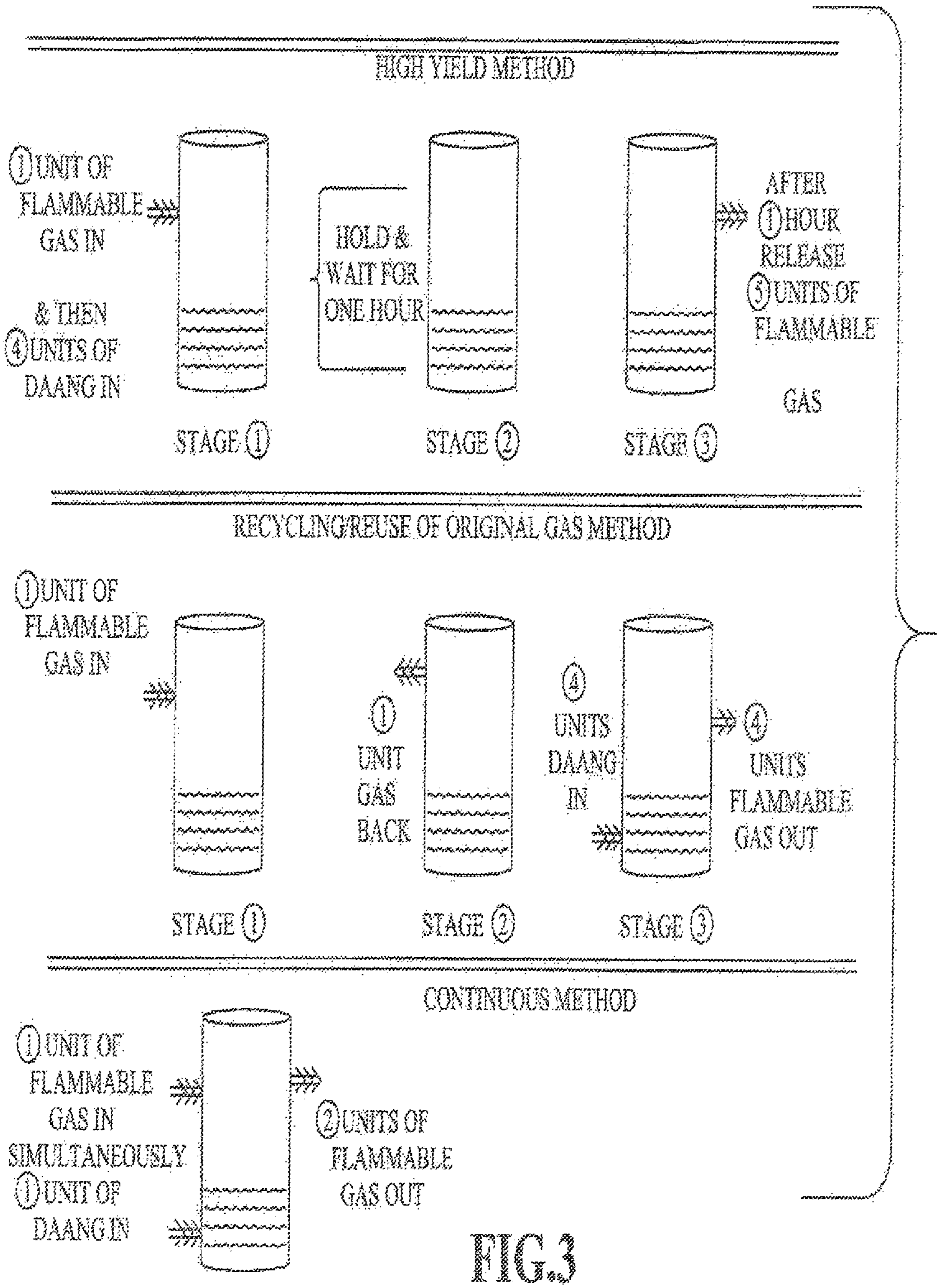
FIG. 3 is a flow chart showing three methods for duplicating a flammable gas.

A system for duplicating flammable gas that produces a flammable gas by use of a process wherein deoxygenated or ambient air or nitrogen gas (DAANG) passes through a specially engineered liquid and escapes in gaseous form to carry out the flammable gas, as shown in the three processes in FIG. 3. The system utilizes an engineered liquid which is exposed to DAANG. The engineered liquid is capable of identifying the composition and arrangement of the introduced flammable gas. After identifying the flammable gas, the engineered liquid is able to duplicate the flammable gas.

A first method, the system comprises the following steps: an engineered liquid is placed in to a container; the engineered liquid is introduced to a flammable gas; the engineered liquid reacts to the flammable gas to alter the engineered liquid's chemical composition and arrangement to mimic the flammable gas's properties to create an altered engineered liquid; the DAANG is introduced to the altered engineered liquid; and the DAANG carries out a flammable gas of the same chemical composition as the introduced flammable gas.

In a particular embodiment, both the DAANG and the flammable gas are added simultaneously, and the amount of duplicated hydrocarbon flammable gas is equal to at least twice the amount originally introduced. The flammable gas is selected from the group consisting of Butane, Cyclobutane, Cycloheptane, Cyclopentane, Cyclopropane, Dimethylpropane, Ethane, Heptane, Hexane, Methane, Methyl Butane, Methanol, Methyl Propane, Pentane, Propane and other hydrocarbon gases.

A variation of the first method: an engineered liquid is introduced to a container; the engineered liquid is introduced to an amount of flammable gas; the engineered liquid reacts to the flammable gas to alter the engineered liquid's chemical composition and arrangement to mimic the flammable gas's properties to create an altered engineered liquid; an amount of DAANG is introduced to the altered engineered liquid; and the DAANG carries out a flammable gas of the same chemical composition as the introduced flammable gas. In a particular embodiment, the volume of the resulting flammable gas is equal to the sum of the volume of the introduced flammable gas and the volume of the introduced DAANG, wherein the flammable gas to DAANG ratio is less than or equal to 1:10.

A second method: an engineered liquid is introduced to a container; the engineered liquid is introduced to a flammable gas; the engineered liquid reacts to the flammable gas to alter the engineered liquid's chemical composition and arrangement to mimic the flammable gas's properties to create an altered engineered liquid; the flammable gas is removed from the container; a DAANG is introduced to the altered engineered liquid; and the DAANG carries out a flammable gas of the same chemical composition as the introduced flammable gas. In a particular embodiment, the flammable gas must be introduced to the engineered liquid for a minimum of ten (10) seconds. In a particular embodiment, the amount of duplicated hydrocarbon flammable gas is equal to at least twice the amount originally introduced.

A third method: an engineered liquid is introduced to a container; the engineered liquid is introduced to an amount of flammable gas; the engineered liquid reacts to the flammable gas to alter the engineered liquid's chemical composition and arrangement to mimic the flammable gas's properties to create an altered engineered liquid; an amount of DAANG is introduced to the altered engineered liquid; the altered engineered liquid, the DAANG and the flammable gas are held in the container for a specified period of time; and the DAANG carries out a flammable gas of the same chemical composition as the introduced flammable gas. In a particular embodiment, the flammable gas and the DAANG must be held in the container for a minimum of thirty (30) minutes.

While the invention has been described in detail and pictorially shown in the accompanying FIG. 1-3 it is not to be limited to such details, since many changes and modifications may be made to the invention without departing from the spirit and the scope thereof. Hence, it is described to cover any and all modifications and forms that may come within the language and scope of the claims.

The invention claimed is:

1. An apparatus for duplicating a flammable gas, the apparatus comprising:

a first container, wherein the first container comprises:

an air inlet comprising a control valve connected to a source of deoxygenated or ambient air or nitrogen gas (DAANG);

a gas inlet comprising a control valve connected to a source of the flammable gas;

an air pressure gauge;

a liquid entrance opening connected to a second container comprising an engineered liquid;

a first gas outlet comprising a control valve configured for release of gas;

a second gas outlet configured to release any remaining gas;

a drainage outlet comprising a control valve;

wherein the engineered liquid is produced by a process comprising:

placing a bacteria mixture into the second container;

adding an algae mixture into the second container;

adding water to the bacteria and algae mixture to create a mutated bacteria solution;

adding a quantity of bone powder or glue;

adding a quantity of sugar or sugar derivative; and allowing the mutated bacteria solution to culture, wherein the first container is configured to react the flammable gas with engineered liquid to mimic the flammable gas's properties and carry out a produced flammable gas of the same chemical composition as the introduced flammable gas.

2. A method for duplicating a flammable gas, the method comprising:

providing a first container, wherein the first container comprises an air inlet, a gas inlet, a liquid entrance opening, and a first gas outlet;

producing an engineered liquid by placing a bacteria mixture into a second container, adding an algae mixture into the second container, adding water to the bacteria and algae mixture to create a mutated bacteria solution, adding a quantity of bone powder or glue, adding a quantity of sugar or sugar derivative, and allowing the mutated bacteria solution to culture;

introducing the flammable gas via the gas inlet and the engineered liquid via the liquid entrance opening to the first container;

reacting the flammable gas to alter the engineered liquid's chemical composition and arrangement to mimic the flammable gas's properties to create an altered engineered liquid in the first container;

introducing deoxygenated or ambient air or nitrogen gas (DAANG) to the altered engineered liquid via the air inlet; and carrying out a flammable gas of the same chemical composition as the introduced flammable gas with the DAANG via the first gas outlet.

* * * * *